United States Patent [19]

Butter et al.

[11] 3,965,208

[45] June 22, 1976

[54] METHYLATION OF TOLUENE

[75] Inventors: Stephen Allan Butter, East Windsor; Warren William Kaeding, Westfield, both of N.J.

[73] Assignee: Mobil Oil Corporation, New York, N.Y.

[22] Filed: Jan. 6, 1975

[21] Appl. No.: 538,666

[52] U.S. Cl. .................. 260/671 M; 208/DIG. 2; 260/671 C; 260/671 R
[51] Int. Cl.² .................. C07C 3/52; C07C 15/08
[58] Field of Search ....... 260/671 R, 671 M, 671 C; 208/DIG. 2

[56] References Cited
UNITED STATES PATENTS

| | | | |
|---|---|---|---|
| 3,277,018 | 10/1966 | Plank et al. | 260/671 |
| 3,367,884 | 2/1968 | Reid | 208/DIG. 2 |
| 3,437,587 | 4/1969 | Ellert et al. | 208/DIG. 2 |
| 3,527,824 | 9/1970 | Pollitzer | 260/671 |
| 3,575,845 | 4/1971 | Miale | 252/430 |
| 3,728,408 | 4/1973 | Tobias | 260/671 |
| 3,751,506 | 8/1973 | Burress | 260/671 |
| 3,755,483 | 8/1973 | Burress | 260/671 |

*Primary Examiner*—Delbert E. Gantz
*Assistant Examiner*—C. E. Spresser
*Attorney, Agent, or Firm*—Charles A. Huggett; Raymond W. Barclay

[57] ABSTRACT

Process for the methylation of toluene under conditions such that the formation of meta-xylene is suppressed and the formation of ortho and para-xylene is enhanced carried out in the presence of a catalyst comprising a crystalline aluminosilicate zeolite, said zeolite having a silica to alumina ratio of at least about 12 and a constraint index, as hereinafter defined, of from 1 to 12, said catalyst having been modified by the addition thereto of a Group VA element in an amount of at least 0.5 percent by weight.

24 Claims, No Drawings

METHYLATION OF TOLUENE

BACKGROUND OF THE INVENTION

1. Field of the Invention

This invention relates to a process for the methylation of toluene in the presence of a crystalline aluminosilicate catalyst modified by the addition thereto of a Group VA element.

2. Description of the Prior Art

Alkylation of aromatic hydrocarbons utilizing crystalline aluminosilicate catalysts has heretofore been described. U.S. Pat. No. 2,904,607 to Mattox refers to alkylation of aromatic hydrocarbons with an olefin in the presence of a crystalline metallic aluminosilicate having uniform pore openings of about 6 to 15 Angstrom units. U.S. Pat. No. 3,251,897 to Wise describes alkylation or aromatic hydrocarbons in the presence of X- or Y-type crystalline aluminosilicate zeolites, specifically such type zeolites wherein the cation is rare earth and/or hydrogen. U.S. Pat. No. 3,751,504 to Keown et al. and U.S. Pat. No. 3,751,506 Burress describe vapor phase alkylation of aromatic hydrocarbons with olefins, e.g. benzene with ethylene, in the presence of a ZSM-5 type zeolite catalyst.

The alkylation of toluene with methanol in the presence of a cation exchanged zeolite Y has been described by Yashima et al. in the Journal of Catalysis 16, 273–280 (1970). These workers reported selective production of para-xylene over the approximate temperature range of 200° to 275°C., with the maximum yield of para-xylene in the mixture of xylenes, i.e., about 50 percent of the xylene product mixture, being observed at 225°C. Higher temperatures were reported to result in an increase in the yield of meta-xylene and a decrease in production of para- and ortho-xylenes.

While the above-noted prior art is considered of interest in connection with the subject matter of the present invention, the methylation process described herein utilizing a catalyst of a crystalline aluminosilicate zeolite having a silica/alumina ratio of at least about 12, a constraint index within the approximate range of 1 to 12 and which has been modified by the addition thereto of a Group VA element in an amount of at least 0.5 percent by weight as described herein, has not, insofar as is known, been heretofore described.

Of the xylene isomers, i.e. ortho-, meta- and para-xylene, meta-xylene is the least desired product, with ortho- and para-xylene being the more desired products. Para-xylene is of particular value being useful in the manufacture of terephthalic acid which is an intermediate in the manufacture of synthetic fibers such as "Dacron". Mixtues of xylene isomers either alone or in further admixture with ethylbenzene, generally containing a concentration of about 24 weight percent para-xylene in the equilibrium mixture, have been previously separated by expensive superfraction and multistage refrigeration steps. Such process, as will be realized, has involved high operation costs and has a limited yield.

SUMMARY OF THE INVENTION

In accordance with the present invention, there has been discovered a process for selectively producing xylenes, without side-product formation of ethylbenzene and mesitylene, by reaction of toluene with a methylating agent in the presence of a catalyst comprising a crystalline aluminosilicate zeolite, said zeolite having a silica to alumina ratio of at least about 12, a constraint index of from 1 to 12 and which has been mofified by the addition thereto of a Group VA element, e.g. phosphorus, arsenic or antimony. In particular, the present process affords selective production of ortho- and para-xylene in preference to meta-xylene and is especially of value in the selective production of para-xylene.

Compared to a conventional thermodynamic equilibrium xylene mixture in which the para:meta:ortho ratio is approximately 1:2:1, the process described herein affords a xylene product in which the ortho- and para-xylenes can approximate 100% of xylene yield and the para-meta-ortho ratio approaches 100:0:0. The improved yield of ortho- and para-xylene and particularly the latter reduces the cost of production and most important the cost of separation of para-xylene from its isomers which is the most expensive step in the current method employed for producing para-xylene.

The present process comprises methylation of toluene in the presence of a particular Group VA element-modified crystalline aluminosilicate catalyst. The catalyst employed is modified by the addition thereto of a Group VA element, e.g. phosphorus, arsenic or antimony in an amount of at least about 0.5 percent by weight. The content of Group VA element may be as high as about 25 percent by weight.

DESCRIPTION OF SPECIFIC EMBODIMENT

The zeolite catalysts herein described are members of a novel class of zeolites exhibiting some unusual properties. These catalysts induce profound transformations of aliphatic hydrocarbons to aromatic hydrocarbons in commerically desirably yields and are generally highly effective in conversion reactions involving aromatic hydrocarbons. Although they have unusually low alumina contents, i.e. high silica to alumina ratios, they are very active even when the silica to alumina ratio exceeds 30. The activity is surprising since catalytic activity is generally attributed to framework aluminum atoms and cations associated with these aluminum atoms. These catalysts retain their crystallinity for long periods in spite of the presence of steam at high temperature which induces irreversible collapse of the framework of other zeolites, e.g. of the X and A type. Furthermore, carbonaceous deposits, when formed, may be removed by burning at higher than usual temperatures to restore activity. In many environments the zeolites of this class exhibit very low coke forming capability, conductive to very long times on stream between burning regenerations.

An important characteristic of the crystal structure of this class of zeolites is that it provides constrained access to, and egress from the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. Briefly, the preferred type catalysts useful in this invention possess, in combination: a silica to alumina ratio of at least about 12; and a structure providing constrained access to the crystalline free space.

The silica to alumina ratio referred to may be determined by conventional analysis. This ratio is meant to represent, as closely as possible, the ratio in the rigid anionic framework of the zeolite crystal and to exclude aluminum in the binder or in cationic or other form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties. It is believed that this hydrophobic character is advantageous in the present invention.

The type zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by 8-membered rings of oxygen atoms, then access by molecules of larger cross-section than normal hexane is excluded and the zeolite is not of the desired type. Windows of 10-membered rings are preferred, although, in some instances, excessive puckering or pore blockage may render these catalysts ineffective. Twelve-membered rings do not generally appear to offer sufficient constraint to produce the advantageous conversions, although puckered structure exist such as TMA offretite which is a known effective zeolite. Also, structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of an equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000°F. for at least 15 minutes. The catalyst is then flushed with helium and the temperature adjusted between 550° and 950°F. to give an overall conversion between 10 and 60%. The mixture of hydrocarbons is passed at 1 liquid hourly space velocity (i.e., 1 volume of liquid hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The constraint index is calculated as follows:

$$\text{Constraint Index} = \frac{\log_{10}(\text{fraction of n-hexane remaining})}{\log_{10}(\text{fraction of 3-methylpentane remaining})}$$

The constraint index approximates the ratio of the cracking rate constants for the two hydrocarbons. Catalysts suitable for the present invention are those having a constraint index in the approximate range of 1 to 12. Constraint Index (CI) values for some typical catalysts are:

| CAS | C.I. |
|---|---|
| ZSM-5 | 8.3 |
| ZSM-11 | 8.7 |
| ZSM-12 | 2 |
| ZSM-21 | 4.5 |
| ZSM-35 | 4.5 |
| TMA Offretite | 3.7 |
| Beta | 0.6 |
| ZSM-4 | 0.5 |
| H-Zeolon | 0.5 |
| REY | 0.4 |
| Amorphous Silica-Alumina | 0.6 |
| Erionite | 38 |

It is to be realized that the above constraint index values typically characterize the specified zeolites but that such are the cumulative result of several variables used in determination and calculation thereof. Thus, for a given zeolite depending on the temperature employed within the aforenoted range of 550° to 950°F., with accompanying conversion between 10 and 60%, the constraint index may vary within the indicated approximate range of 1 to 12. Likewise, other variables such as the crystal size of the zeolites, the presence of possibly occluded contaminants and binders intimately combined with the zeolite may affect the constraint index. It will accordingly be understood by those skilled in the art that the constraint index, as utilized herein, while affording a highly useful means for characterizing the zeolites of interest is approximate, taking into consideration the manner of its determination, with the probability, in some instances, of compounding variable extremes. However, in all instances, at a temperature within the above-specified range of 550° to 950°F., the constraint index will have a value for any given zeolite of interest herein within the approximate range of 1 to 12.

The class of zeolites defined herein is exemplified by ZSM-5, ZSM-11, ZSM-12, ZSM-21, ZSM-35 and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in U.S. Pat. No. 3,832,449, the entire contents of which are incorporated herein by reference.

ZSM-21 is more particularly described in U.S. application Ser. No. 560,412, filed Mar. 20, 1975. This zeolite can be identified, in terms of mole ratios of oxides and in the anhydrous state, as follows:

$$(0.3-2.5)R_2O : (0-0.8)M_2O : Al_2O_3 : > 8\ SiO_2$$

wherein R is an organic nitrogen-containing cation derived from a 2-(hydroxyalkyl) trialkylammonium compound and M is an alkali metal cation, and is characterized by a specified X-ray powder diffraction pattern.

In a preferred synthesized form, the zeolite has a formula, in terms of mole ratios of oxides and in the anhydrous state, as follows:

$$(0.4-2.5)R_2O : (0-0.6)\ M_2O : Al_2O_3 : xSiO_2$$

wherein R is an organic nitrogen-containing cation derived from a 2-(hydroxyalkyl)trialkylammonium compound, wherein alkyl is methyl, ethyl or a combination thereof, M is an alkali metal, especially sodium, and x is from greater than 8 to about 50.

The synthetic ZSM-21 zeolite possesses a definite distinguishing crystalline structure whose X-ray diffraction pattern shows substantially the significant lines set forth in Table I. It is observed that this X-ray diffraction pattern (significant lines) is similar to that of natural ferrierite with a notable exception being that natural ferrierite patterns exhibit a significant line at 11.33A.

TABLE I

| d(A) | I/Io |
|---|---|
| 9.8 ± 0.20 | Strong |
| 9.1 ± 0.19 | Medium |
| 8.0 ± 0.16 | Weak |
| 7.1 ± 0.14 | Medium |
| 6.7 ± 0.14 | Medium |
| 6.0 ± 0.12 | Weak |
| 4.37 ± 0.09 | Weak |
| 4.23 ± 0.09 | Weak |
| 4.01 ± 0.08 | Very Strong |
| 3.81 ± 0.08 | Very Strong |
| 3.69 ± 0.07 | Medium |
| 3.57 ± 0.07 | Very Strong |
| 3.51 ± 0.07 | Very Strong |
| 3.34 ± 0.07 | Medium |
| 3.17 ± 0.06 | Strong |
| 3.08 ± 0.06 | Medium |
| 3.00 ± 0.06 | Weak |
| 2.92 ± 0.06 | Medium |
| 2.73 ± 0.06 | Weak |
| 2.66 ± 0.05 | Weak |
| 2.60 ± 0.05 | Weak |
| 2.49 ± 0.05 | Weak |

A further characteristic of ZSM-21 is its sorptive capacity providing said zeolite to have increased capacity for 2-methylpentane (with respect to n-hexane sorption by the ratio n-hexane/2-methyl-pentane) when compared with a hydrogen form of natural ferrierite resulting from calcination of an ammonium exchanged form. The characteristic sorption ratio n-hexane/2-methylpentane for ZSM-21 (after calcination at 600°C.) is less than 10, whereas that ratio for the natural ferrierite is substantially greater than 10, for example, as high as 34 or higher.

Zeolite ZSM-21 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| R+ | Broad | Preferred |
|---|---|---|
| R+ + M+ | 0.2–1.0 | 0.3–0.9 |
| OH⁻/SiO₂ | 0.05–0.5 | 0.07–0.49 |
| H₂O/OH⁻ | 41–500 | 100–250 |
| SiO₂/Al₂O₃ | 8.8–200 | 12–60 | wherein R is an organic nitrogen-containing cation derived from a 2-(hydroxyalkyl) trialkylammonium compound and M is an alkali metal ion, and maintaining the mixture until crystals of the zeolite are formed. (The quantity of OH⁻ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is thereafter dried, e.g. at 230°F. for from about 8 to 24 hours.

ZSM-35 is more particularly described in U.S. application Ser. No. 528,06, filed Nov. 12, 1974. This zeolite can be identified, in terms of mole ratios of oxides and in the anhydrous state, as follows:

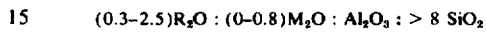

$(0.3-2.5)R_2O : (0-0.8)M_2O : Al_2O_3 : > 8 SiO_2$ wherein R is an organic nitrogen-containing cation derived from ethylenediamine or pyrrolidine and M is an alkali metal cation, and is characterized by a specified X-ray powder diffraction pattern.

In a preferred synthesized form, the zeolite has a formula, in terms of mole ratios of oxides and in the anhydrous state, as follows:

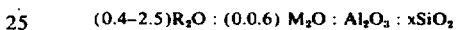

$(0.4-2.5)R_2O : (0.0.6) M_2O : Al_2O_3 : xSiO_2$ wherein R is an organic nitrogen-containing cation derived from ethylenediamine or pyrrolidine, M is an alkali metal, especially sodium, and x is from greater than 8 to about 50.

The synthetic ZSM-35 zeolite possesses a definite distinguishing crystalline structure whose X-ray diffraction pattern shows substantially the significant lines set forth in Table II. It is observed that this X-ray diffraction pattern (with respect to significant lines) is similar to that of natural ferrierite with a notable exception being that natural ferrierite patterns exhibit a significant line at 11.33A. Close examination of some individual samples of ZSM-35 may show a very weak line at 11.3–11.5A. This very weak line, however, is determined not to be a significant line for ZSM-35.

TABLE II

| d(A) | I/Io |
|---|---|
| 9.6 ± 0.20 | Very Strong – Very Very Strong |
| 7.10 ± 0.15 | Medium |
| 6.98 ± 0.14 | Medium |
| 6.64 ± 0.14 | Medium |
| 5.78 ± 0.12 | Weak |
| 5.68 ± 0.12 | Weak |
| 4.97 ± 0.10 | Weak |
| 4.58 ± 0.09 | Weak |
| 3.99 ± 0.08 | Strong |
| 3.94 ± 0.08 | Medium Strong |
| 3.85 ± 0.08 | Medium |
| 3.78 ± 0.08 | Strong |
| 3.74 ± 0.08 | Weak |
| 3.66 ± 0.07 | Medium |
| 3.54 ± 0.07 | Very Strong |
| 3.48 ± 0.07 | Very Strong |
| 3.39 ± 0.07 | Weak |
| 3.32 ± 0.07 | Weak Medium |
| 3.14 ± 0.06 | Weak Medium |
| 2.90 ± 0.06 | Weak |
| 2.85 ± 0.06 | Weak |
| 2.71 ± 0.05 | Weak |
| 2.65 ± 0.05 | Weak |
| 2.62 ± 0.05 | Weak |
| 2.58 ± 0.05 | Weak |
| 2.54 ± 0.05 | Weak |
| 2.48 ± 0.05 | Weak |

A further characteristic of ZSM-35 is its sorptive capacity proving said zeolite to have increased capacity for 2-methylpentane (with respect to n-hexane sorption by the ratio n-hexane/2-methylpentane) when compared with a hydrogen form of natural ferrierite resulting from calcination of an ammonium exchanged form. The characteristic sorption ration n-hexane/2-methylpentane for ZSM-35 (after calcination at 600°C.) is less than 10, whereas that ratio for the natural ferrierite is substantially greater than 10, for example, as high as 34 or higher.

Zeolite ZSM-35 can be suitably prepared by preparing a solution containing sources of an alkali metal oxide, preferably sodium oxide, an organic nitrogen-containing oxide, an oxide of aluminum, an oxide of silicon and water and having a composition, in terms of mole ratios of oxides, falling within the following ranges:

| $R+$ | Broad | Preferred |
|---|---|---|
| $R+ + M+$ | 0.2–1.0 | 0.3–0.9 |
| $OH^-/SiO_2$ | 0.05–0.5 | 0.07–0.49 |
| $H_2O/OH^-$ | 41–500 | 100–250 |
| $SiO_2/Al_2O_3$ | 8.8–200 | 12–60 | wherein R is an organic nitrogen-containing cation derived from pyrrolidine or ethylenediamine and M is an alkali metal ion, and maintaining the mixture until crystals of the zeolite are formed. (The quantity of $OH^-$ is calculated only from the inorganic sources of alkali without any organic base contribution). Thereafter, the crystals are separated from the liquid and recovered. Typical reaction conditions consist of heating the foregoing reaction mixture to a temperature of from about 90°C. to about 400°C. for a period of time of from about 6 hours to about 100 days. A more preferred temperature range is from about 150°C. to about 400°C. with the amount of time at a temperature in such range being from about 6 hours to about 80 days.

The digestion of the gel particles is carried out until crystals form. The solid product is separated from the reaction medium, as by cooling the whole to room temperature, filtering and water washing. The crystalline product is dried, e.g. at 230°F., for from about 8 to 24 hours.

The specific zeolites described, when prepared in the presence of organic cations, are catalytically inactive, possibly because the intracrystalline free space is occupied by organic cations from the forming solution. They may be activated by heating in an inert atmosphere at 1000°F. for 1 hour, for example, followed by base exchange with ammonium salts followed by calcination at 1000°F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000°F. for from about 15 minutes to about 24 hours.

Natural zeolites may sometimes be converted to this type zeolite catalyst by various activation procedures and other treatments such as base exchange, steaming, alumina extraction and calcination, in combinations. Natural minerals which may be so treated include ferrierite, brewsterite, stilbite, dachiardite, epistilbite, heulandite and clinoptilolite. The preferred crystalline aluminosilicates are ZSM-5, ZSM-11, ZSM-12, ZSM-21 and ZSM-35, with ZSM-5 particularly preferred.

The catalysts of this invention may be in the hydrogen form or they may be base exchanged or impregnated to contain ammonium or a metal cation complement. It is desirable to calcine the catalyst after base exchange. The metal cations that may be present include any of the cations of the metals of Groups 1 through VIII of the periodic table. However, in the case of Group IA metals, the cation content should in no case be so large as to effectively inactivate the catalyst.

In a preferred aspect of this invention, the catalysts hereof are selected as those having a crystal framework density, in the dry hydrogen form, of not substantially below about 1.6 grams per cubic centimeter. It has been found that zeolites which satisfy all three of these criteria are most desired because they tend to maximize the production of gasoline boiling range hydrocarbon products. Therefore, the preferred catalysts of this invention are those having a constraint index as defined above of about 1 to about 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g., on page 19 of the article on Zeolite Structure by W. M. Meir. This paper, the entire contents of which are incorporated herein by reference, is included in "Proceedings of the Conference on Molecular Sieves, London, April 1967", published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density, of course, must be associated with a relatively small amount of free space within the crystal, which might be expected to result in more stable structres. This free space, however, is important as the locus of catalytic activity.

Crystal framework densities of some typical zeolites are:

| Zeolite | Void Volume | Framework Density |
|---|---|---|
| Ferrierite | 0.28 cc/cc | 1.76 g/cc |
| Mordenite | .28 | 1.7 |
| ZSM-5, -11 | .29 | 1.79 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite wherein the original alkali metal has been reduced to less than about 1.5 percent by weight may be used. Thus, the original alkali metal of the zeolite may be replaced by ion exchange with other suitable ions of Groups IB to VIII of the Periodic Table including, by way of example, nickel, zinc, calcium or rare earth metals.

The crystals of zeolite in a form substantially free of alkali metal, i.e. containing less than about 1.5 weight percent alkali metal and preferably having at least a portion of the original cations associated therewith replaced by hydrogen, are then contacted with a Group VA element or compound thereof and preferably a phosphorus compound.

Representative suitable Group VA compounds are those of phosphorus, antimony and arsenic. Representative phosphorus-containing compounds include derivatives of groups represented by $PX_3$, $RPX_2$, $R_2PX$, $R_3P$, $R_3P=O$, $R_3P=S$, $RPO_2$, $PPS_2$, $RP(OXOX)_2$, $RP(S)(SX)_2$, $R_2P(O)OX$, $R_2P(S)SX$, $RP(OX)_2$, $RP(SX)_2$, $ROP(OX)_2$, $PSP(SX)_2$, $(RS)_2PSP(SR)_2$, and $(RO)_2POP(OR)_2$, where R is an alkyl or aryl, such as a phenyl radical and X is hydrogen, R, or halide. These compounds include primary, $RPH_2$, secondary, $R_2PH$ and tertiary, $R_3P$, phosphines such as butyl phosphine; the tertiary phosphine oxides $R_3PO$, such as tributylphosphine oxide, the tertiary phosphine sulfides, $R_3PS$, the primary, $RP(O)(OX)_2$, and secondary, $R_2P(O)(OX)$, phosphonic acids such as benzene phosphonic acid; the corresponding sulfur derivatives such as $RP(S)(SX)_2$ and $R_2P(S)SX$, the esters of the phosphonic acids such as diethyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites; and esters thereof such as the monopropyl ester, alkyl dialkylphosphinites, $(RO)PR_2$, and dialkyl alkylphosphonite, $(RO)_2PR$ esters. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$ and $(RS)_2PR$. Examples of phosphite esters include trimethylphosphite, triethylphosphite, diisopropylphosphite, butylphosphite; and pyrophosphites such as tetraethylpyrophosphite. The alkkyl groups in the mentioned compounds contain one to four carbon atoms.

Other suitable phosphorus-containing compounds include the phosphorus halides such as phosphorus trichloride, bromide, and iodide, alkyl phosphorodichloridites, $(RO)PCl_2$, dialkyl phosphorochloridites, $(RO)_2PX$, dialkylphosphinochloridites, $R_2PCl$, alkyl alkylphosphonochloridates, $(RO)(R)P(O)Cl$, and dialkyl phosphinochloridates, $R_2P(O)Cl$. Applicable corresponding sulfur derivatives include $(RS)PCl_2$, $(RS)_2PX$, $(RS)(R)P(S)Cl$ and $R_2P(S)Cl$.

preferred phosphorus-containing compounds include diphenyl phosphine chloride, trimethylphosphite and phosphorus trichloride, phosphoric acid, phenyl phosphine oxychloride, trimethylphosphate, diphenyl phosphinous acid, diphenyl phosphinic acid and diethylchloro thiophosphate.

Some typical, non-limiting examples of arsenic and antimony derivatives which may be utilized within the scope of this invention include: the hydrides, $AsH_3$, $SbH_3$; halides of formulas $MX_3$, $MX_5$ (M = As, Sb, X = F, Cl, Br, I); organic derivatives such as alkyl and aryl arsines and stibines, and their oxides such as $R_3As$, $R_5As$, $R_3Sb$, $R_5Sb$, $R_rSb = O$ and $R_rAs = O$; halogen derivatives, $RAsX_2$, $R_2AsX$, $RAsX_4$, $R_2AsX_3$, $R_3AsX_2$, $R_4AsX$, $RSbX_2$, $R_2SbX$, $RSbX_4$, $R_2SbX_3$, $R_3SbX_2$, $R_4SbX$; the acids $H_3AsO_3$, $HAsO_2$, $HAsO_3$, $H_3AsO_4$, $H_4As_2O_7$, $H_3SbO_3$, $HSbO_2$, $HSb(OH)_6$; organic-substituted acids such as $RSbO(OH)_2$, $R_2SbO·OH$, $RAsO(OH)_2$, $RAsO·OH$, where R and X have the same significance as indicated hereinabove. Other suitable compounds include organic ethers such as $R_2SbOSbR_2$; esters and alcoholates such as $Sb(OOCH_3)_3$, $Sb(OC_4H_9)_3$, $Sb(OC_2H_5)_3$, $Sb(OCH_3)_3$, $As(OC_2H_5)_3$, $As(OCH_3)_3$. Also included would be arsenite salts such as $Na_3AsO_3$, $KAsO_2$, $Na_2As_4O_7$, and antimonyl salts as $(SbO)SO_4$, $(SbO)NO_3$, $K(SbO)C_4H_4O_6$, $NaSbO_2 · 3H_2O$.

Incorporation of the Group VA element with the zeolite provides a composition having unique properties as a catalytic agent. Thus, the so treated zeolite possesses a greater number of acid sites than the parent zeolite but these sites appear to have a lesser acid strength than those found in the parent zeolite. It is believed that the apparent replacement of the strong acid sites with a greater number of relatively weak acid sites may be responsible for the unique catalytic properties of the Group VA element-containing zeolite.

Reaction of the zeolite with the Group VA-containing compound is effected by contacting the zeolite with such compound. Where the treating Group VA compound is a liquid, such compound can be in solution in a solvent at the time contact with the zeolite is effected. Any solvent relatively inert with respect to the treating compound and the zeolite may be employed. Suitable solvents include aliphatic, aromatic or alcoholic liquids. Where the Group VA-containing compound is, for example, trimethylphosphite or liquid phosphorus trichloride, a hydrocarbon solvent such as n-octane may be employed. The Group VA-containing compound may be used without a solvent, i.e., may be used as a neat liquid. Where the Group VA-containing compound is in the gaseous phase, such as where gaseous phosphorus trichloride is employed, the treating compound can be used by itself or can be used in admixture with a gaseous diluent relatively inert to the Group VA-containing compound and the zeolite such as air or nitrogen.

Preferably, prior to reacting the zeolite with the Group VA-containing compound, the zeolite is dried. Drying can be effected in the presence of air. Elevated temperatures may be employed. However, the temperature should not be such that the crystal structure of the zeolite is destroyed.

Heating of the Group VA-containing catalyst subsequent to preparation and prior to use is also preferred. The heating can be carried out in the presence of oxygen, for example air. Heating can be at a temperature of about 150°C. However, higher temperatures, i.e., up to about 500°C. are preferred. Heating can be carried out for 3–5 hours. It has been found that heating increases the catalyst efficiency of the Group VA element-containing zeolite, probably due to an increase in the number of acid sites rather than an increase in the strength of the existing acid sites. Increasing the heating temperature increases the catalyst efficiency. However, while heating temperatures above about 500°C. can be employed, they are not necessary. At temperatures of about 1000°C., the crystal structure of the zeolite tends to deteriorate.

The amount of Group VA element incorporated with the zeolite should be at least about 0.5 percent by weight. With this amount of Group VA element, replacement of a sufficient proportion of the strong acid sites of the zeolite with an increased number of weak acid sites is effected. However, it is preferred in order to increase the replacement of the strong acid sites with an increased number of these weaker acid sites that the amount of Group VA element in the zeolite be at least about 2 percent by weight. The amount of Group VA element can be as high as about 25 percent by weight. When phosphorus is the Group VA element, the amount added to the zeolite is preferably between about 2 and about 15 percent by weight. With arsenic and antimony, the preferred amounts are within the approximate range of 1 to 10 weight percent.

The amount of Group VA incorporated with the zeolite by reaction with the Group VA element or Group VA-containing compound will depend upon several factors. One of these is the reaction time, i.e., the time that the zeolite and the Group VA-containing source are maintained in contact with each other. With greater reaction times, all other factors being equal, a greater amount of Group VA element is incorporated with the zeolite. Another factor is the ratio of the Group VA element or Group VA-containing compound to the zeolite in the reaction mixture employed to effect incorporation of the Group VA element with the zeolite. With greater ratios of Group VA element-containing compound to zeolite, again all other factors being equal, a greater amount of Group VA element is incorporated with the zeolite. Other factors upon which the amount of Group VA element incorporated with the zeolite is dependent include reaction temperature, concentration of the treating compound in the reaction mixture, the degree to which the zeolite has been dried prior to reaction with the Group VA element-containing compound and the conditions of drying of the zeolite after reaction of the zeolite with the treating compound.

It has been found that the concentration of Group VA element-induced weak acid sites, and thus the catalytic activity, of the phosphorus-containing zeolite is altered upon contact with water vapor. Thus, upon contact with water vapor the number of weak acid sites appears to be increased. This increase may occur after the Group VA element-containing zeolite is put into use as a catalyst as a result of contact with water vapor contained in the feed to the catalyst or formed during the reaction of the feed with the catalyst. Preferably, however, in order to obtain the benefits of an initial increased catalytic activity of the Group VA element-containing zeolite, the same is contacted with water vapor prior to its use as a catalyst. Contact of such zeolite with the water vapor may be carried out in any suitable manner. For example, sorption of water vapor on the Group VA element-containing zeolite can be effected in a vacuum desiccator at ambient conditions for one hour. Water vapor can also be sorbed by passing an inert gas such as helium through a water bubbler and passing the entrained water vapor through the Group VA element-containing zeolite in a reaction tube. Other methods of contacting the Group VA element-containing zeolite with water involve co-feeding an alcohol or ether compound during a hydrocarbon conversion catalytic reaction. These materials as well as other oxygen-containing compounds generate water in-situ during reaction and maintain the catalyst in an active form. Water vapor or water vapor diluted with an inert gas may also be used to maintain activity of the catalyst.

In practicing the desired methylation process it may be desirable to incorporate the modified zeolite in another material resistant to the temperatures and other conditions employed in the methylation process. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the modified zeolite include those of the montmorillonite and kaolin families, which families include the sub-bentonites and the kaolins commonly known as Dixie, McNamee-Georgia and Florida clays or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the modified zeolites employed herein may be composited with a porous matrix material, such as silica-alumina, silica-magnesia, silica-zirconia, silica-thoria, silica-berylia, silica-titania as well as ternary compositions, such as silica-alumina-thoria, silica-alumina-zirconia, silica-alumina-magnesia and silica-magnesia-zirconia. The matrix may be in the form of a cogel. The relative proportions of finely divided modified zeolite and inorganic oxide gel matrix may vary widely with the zeolite content ranging from between about 1 to about 99 percent by weight and more usually in the range of about 5 to about 80 percent by weight of the composite.

Methylation of toluene in the presence of the abovedescribed catalyst is effected by contact of the toluene with a methylating agent, preferably methanol, at a temperature between about 250°C. and about 750°C. and preferably between about 500°C. and about 700°C. At the higher temperatures, the zeolites of high silica/alumina ration are preferred. For example, ZSM-5 of 300 $SiO_2/Al_2O_3$ ratio and upwards is very stable at high temperatures. The reaction generally takes place at atmospheric pressure, but the pressure may be within the approximate range of 1 atmosphere to 1000 psig. The molar ratio of methylating agent to toluene is generally between about 0.05 and about 5. When methanol is employed as the methylating agent a suitable molar ratio of methanol to toluene has been found to be approximately 0.1–2 moles of methanol per mole of toluene. With the use of other methylating agents, such as methylchloride, methylbromide, dimethylether, methyl carbonate, light olefins or dimethylsulfide, the molar ratio of methylating agent to toluene may vary within the aforenoted range. Reaction is suitably accomplished utilizing a weight hourly space velocity of between about 1 and about 2000 and preferably between about 5 and about 1500. The reaction product consisting predominantly of para-xylene or a mixture of para- and ortho-xylene together with comparatively smaller amounts of meta-xylene may be separated by any suitable means, such as by passing the same through a water condenser and subsequently passing the organic phase through a column in which chromatographic separation of the xylene isomers is accomplished.

The process of this invention may be carried out as a batch-type, semi-continuous or continuous operation utilizing a fixed or moving bed catalyst system. A preferred embodiment entails use of a fluidized catalyst zone wherein the reactants, i.e. toluene and methylating agent, are passed concurrently or countercurrently through a moving fluidized bed of the catalyst. The fluidized catalyst after use is conducted to a regeneration zone wherein coke is burned from the catalyst in an oxygen-containing atmosphere, e.g. air, at an elevated temperature, after which the regenerated catalyst is recycled to the conversion zone for further contact with the toluene and methylating agent reactants.

Reactivation of the Group VA modified zeolite catalyst can be effected by passing a vaporized Group VA compound, e.g. a phosphorus compound, through the catalyst bed after the catalyst has been used for the desired methylation of toluene to para-xylene. Thus, for example, after a period of continued use of the catalyst, it can be revivified by passage therethrough of a vaporized mixture, e.g. an equal volume mixture, of toluene and diphenyl phosphine chloride at an elevated temperature, i.e. about 250°C. over a one-half hour period of time. This treatment is then suitably followed by heating in air at 150 cc/minute at about 550°C. for approximately one-half hour.

The following examples will serve to illustrate the process of this invention without limiting the same:

EXAMPLE 1

This example illustrates the preparation of phosphorus-containing zeolites.

Several preparations of crystalline aluminosilicate zeolites were combined to form a composite. Each of these aluminosilicate zeolites was ZSM-5 containing sodium as the cation associated therewith and had been prepared by conventional techniques employing tetrapropylammonium hydroxide. The composite had a silica to alumina ratio of 70 and the individual zeolite catalysts had components falling in the ranges: 1.1–1.4% Na, 4.22–7.31% C, 0.39–0.63% N, 2.25–2.45% $Al_2O_3$, and 91.3–95.0% $SiO_2$. The C/N atomic ratio was 12.5–13.5 and the Na/Al ratio was approximately 1.2.

The composite, in powder form, was brought to a temperature of 540°C. under a stream of nitrogen (the heating rate was about 2.5°C. per minute) and held for 16 hours to remove residue of the tetrapropylammonium hydroxide. It was then pressed into wafers, crushed, and screened to 8–12 mesh, followed by ion exchange with 0.5 N $NH_4NO_3$, the $NH_4^+$ replacing the $Na^+$. The resulting pellets were air-dried and calcined in air at 500°C. for 3–16 hours whereby $H^+$ replaced the $NH_4^+$ to yield HZSM-5.

A 10-gram sample of HZSM-5 so prepared was added to 3.94 cubic centimeters of trimethylphosphite dissolved in 50 cubic centimeters of n-octane in a flask. Under a slow stream of nitrogen the mixture was heated to reflux temperature (about 120°C.) for 72 hours. A ten-inch vigreaux column was added to the flask for distillation and 21 grams of liquid were collected at 90°–113°C. for subsequent analysis. The solids were filtered and washed with 100 cubic centimeters each of pentane, methylene chloride, and pentane. They were then air-dried followed by drying in a vacuum oven overnight at 110°C. They were next pressed into wafers, broken and screened to 8–12 mesh size and heated in air at 500°C. for 3 hours. The resulting product was the phosphorus-containing zeolite.

The above procedure was repeated with ten other samples with variations in the ratio of trimethylphosphite to zeolite and reaction time, i.e., time of contact of the trimethylphosphite with the zeolite. One of the samples was heated at 300°C. rather than at 500°C. Another one of the samples was treated with a large excess of neat trimethylphosphite, i.e., without any n-hexane solvent.

A portion of each of the phosphorus-containing zeolites was analyzed by X-ray. The results are listed in Table I in weight percent and are calculated on a dry weight basis after a heating of about 0.5 hour at 1000°–1100°C. For comparison purposes, there is included an analysis of the zeolite, identified in the table as Sample 1, prior to conversion to a phosphorus-containing zeolite. Sample 6 was the sample heated at 300°C. Sample 11 was the sample treated with a large excess of neat trimethylphosphite. The weight loss is the thermal gravimetric weight loss and was determined at 900°C. by standard techniques using a basic DuPont Model instrument. Most of the weight loss indicated in the table was found to be due to water although traces of organic material (~0.5–2%) were also noted in effluent gases.

TABLE I

| Sample | % P  | % $Al_2O_3$ | % $SiO_2$ | Reaction Time, Hrs. | Weight Loss |
|--------|------|-------------|-----------|---------------------|-------------|
| 1      | 0    | 2.20        | 94.9      | —                   | 3.0         |
| 2      | 4.51 | 2.03        | 89.5      | 72                  | 8.0         |
| 3      | 4.42 | 2.21        | 93.1      | 66                  | 8.7         |
| 4      | 3.72 | 2.03        | 91.8      | 16                  | 8.0         |
| 5      | 3.21 | 2.00        | 94.2      | 17                  | 7.0         |
| 6      | 3.30 | 1.94        | 92.1      | 17                  | 3.4         |
| 7      | 3.77 | 1.96        | 93.2      | 16                  | —           |
| 8      | 4.08 | 1.85        | 91.0      | 16                  | 2.7         |
| 9      | 0.78 | 2.22        | 94.4      | 16                  | 6.5         |
| 10     | 1.45 | 2.08        | 95.7      | 16                  | 4.5         |
| 11     | 2.68 | 1.91        | 88.7      | 16                  | ~1          |

EXAMPLE 2

This example will further illustrate the preparation of a phosphorus-containing zeolite.

Six grams of HZSM-5 zeolite were placed in a flask fitted with a thermometer, a nitrogen purge, a reflux condenser, a dropping funnel, and a calcium chloride trap on the nitrogen exit line leading from the top of the flask. The zeolite was heated to 230°–240°C. for about 2 hours while nitrogen was passed through the flask to remove moisture. After allowing the zeolite to cool, 50 cubic centimeters of phosphorus trichloride from the dropping funnel were added to the zeolite. The surface of the zeolite turned a light yellow-orange color immediately. The slurry of zeolite and phosphorus trichloride was carefully refluxed for 20 hours.

After cooling, the phosphorus-containing zeolite was filtered off, washed with 150 cubic centimeters of chloroform, and dried in a vacuum oven at 110°C. It was then placed in a quartz tube with a thermowell in the center and heated to 130°–140°C. Nitrogen saturated with water at 30°–50°C. was passed through the tube for 20 hours. Hydrogen chloride was evolved in the process.

The phosphorus-containing zeolite was then heated at 150°C. in dry nitrogen. Analysis of this zeolite indicated that it contained 2.95 percent by weight of phosphorus.

Analyses of the phosphorus-containing zeolites were made by X-ray prior and subsequent to being used as the catalysts and the results are given in Table II.

TABLE II

| Sample No. | % P | | % Al$_2$O$_3$ | | % SiO$_2$ | | Reaction Conditions | |
|---|---|---|---|---|---|---|---|---|
| | Fresh | Used | Fresh | Used | Fresh | Used | Time | Temperature |
| 4 | 3.72 | 3.67 | 2.03 | 2.02 | 91.8 | 87.4 | 14 hrs. | 250–400°C. |
| 6 | 3.30 | 3.53 | 1.94 | 1.99 | 92.1 | 88.7 | 6 hrs. | 250–500°C. |
| 7 | 3.77 | 3.64 | 1.96 | 1.90 | 93.2 | 97.4 | 23 hrs. | 350–500°C. |

EXAMPLE 3

This example will still further illustrate the preparation of a phosphorus-containing zeolite.

Seven grams of HZSM-5 zeolite were placed in a quartz tube fitted with a thermowell in the center. The zeolite was heated in dry nitrogen at 500°C. for 1.5 hours to remove moisture. After cooling to 300°C., 44 grams of phosphorus trichloride vapor were passed through the zeolite over a period of 3 hours. Nitrogen was used as a carrying gas. The system was carefully protected from moisture.

After this treatment, air was substituted for the nitrogen and was passed over the zeolite at a rate of 100 cubic centimeters per minute for 16 hours and at a temperature of 400°C. Analysis of the resulting phosphorus-containing zeolite indicated that it contained 1.38 percent by weight of phosphorus.

EXAMPLE 4

This example will illustrate still another method of preparing a phosphorus-containing zeolite.

In an apparatus similar to that described in Example 2, 15.0 grams of dry HZSM-5 zeolite were refluxed with 100 cubic centimeters of neat trimethylphosphite for 20 hours. After cooling, the zeolite was filtered off, washed with methylene chloride followed by pentane, pumped down in a vacuum oven, and heated in air at 500°C. for 22 hours. The total dry weight after heating was 15.8 grams. Analysis of the phosphorus-containing zeolite indicated that it contained 2.68 percent by weight of phosphorus.

EXAMPLE 5

This example will illustrate another method of preparing a phosphorus-containing zeolite.

In a manner similar to that described in Example 3, 8.8 grams of HZSM-11 zeolite were treated with 74 grams of an equivolume solution of phosphorus trichloride and cyclohexane at 300°–450°C. over a period of 3.3 hours.

EXAMPLE 6

This example will illustrate the stability of the phosphorus-containing zeolite under conditions of use as a catalyst.

The phosphorus-containing zeolites identified in Example 1 as Samples 4, 6 and 7 were each used as catalysts for conversion reactions. The conversion in which Sample 7 was employed was carried out in the presence of water vapor. In the reaction in which Sample 4 was employed, the phosphorus-containing zeolite was regenerated two times during the reaction by calcining in air at 500°C. In the reactions in which Samples 6 and 7 were employed, the phosphorus-containing zeolites were similarly regenerated 1 time and 4 times, respectively.

It will be observed from Table II that the compositions of the phosphorus-containing zeolites were substantially unaltered, particularly as to phosphorus content, by use as a catalyst and by regeneration. The absence of loss of phosphorus indicates a strong bonding of the phosphorus with the zeolite.

EXAMPLE 7

This example will demonstrate the lack of effect of the incorporation of the phosphorus with the zeolite on the unit cell dimensions of the zeolite and the decrease in the relative intensities of the 11.10 and 9.95 A d-spacings by the incorporation of the phosphorus with the zeolite.

One ZSM-5 zeolite without phosphorus and four phosphorus-containing ZSM-5 zeolites, each of the phosphorus-containing zeolites containing a different amount of phosphorus, were subjected to X-ray analysis to determine their definitive X-ray diffraction patterns. The patterns were measured automatically by a proportional counter diffractometer using CuK $\alpha$ (doublet) radiation. Peak height, I, and band position as a function of 2θ were used to calculate relative intensities (100 I/Io), where I is the strongest line intensity and (d obs) the interplanar spacings in angstroms. Table III compares the relative intensities of the seven major d-spacings as a function of phosphorus concentration.

It will be observed from Table III that the d-spacings are essentially identical for the zeolite without phosphorus and the phosphorus-containing zeolite. It will also be observed that there was a decrease in the relative intensities of the interplanar spacings at d=11.10A and d=9.95A of the phosphorus-containing zeolite and the decrease was in a linear manner proportional to the amount of the phosphorus. The d-spacings of the zeolite without phosphorus and the phosphorus-containing zeolite being essentially identical are indicative that the phosphorus is not present as a constituent of the crystalline framework of the phosphorus-containing zeolite. It will be further observed that, with an amount of phosphorus of 0.78 percent by weight, the decrease in the 11.10 and 9.95A d-spacings was at least 15 percent.

TABLE III

| d obs A° | Wt % Phosphorus | Relative Intensity, 100 I/Io | | | | |
|---|---|---|---|---|---|---|
| | | 0 | 0.78 | 1.45 | 3.93 | 4.15 |
| 11.100 | | 87 | 71 | 63 | 35 | 28 |
| 9.950 | | 58 | 48 | 42 | 20 | 22 |
| 3.837 | | 100 | 100 | 100 | 100 | 100 |
| 3.808 | | 68 | 73 | 72 | 69 | 66 |
| 3.742 | | 37 | 41 | 42 | 39 | 40 |
| 3.708 | | 49 | 53 | 51 | 53 | 50 |
| 3.639 | | 28 | 30 | 29 | 25 | 27 |

EXAMPLE 8

Employing the catalyst of Example 1 (Sample 5), toluene and dimethylether were reacted utilizing a feed wherein the molar ratio of toluene to dimethyl ether was 1.4. This feed was passed over 5 grams of the catalyst at a weight hourly space velocity of 5. at a temperature of 450°C. for a period of 350 minutes. Conversion of toluene was 61 percent. Xylene production amounted to 32.7 percent with the para:meta:ortho weight ratio being 30.2:45.7:24.1.

EXAMPLES 9–15

These examples were carried out in a manner similar to that for Example 8 but at differing temperatures and for different reaction times. Results are shown in the table below.

| Example | 9 | 10 | 11 | 12 | 13 | 14 | 15 |
|---|---|---|---|---|---|---|---|
| Temp. °C. | 250 | 275 | 300 | 300 | 350 | 400 | 400 |
| Time On-Stream (Min.) | 860 | 920 | 60 | 440 | 320 | 135 | 290 |
| % Conversion of Toluene | 3.6 | 7.0 | 2.2 | 14.2 | 34.8 | 40.5 | 54.1 |
| Xylene Production, % | 1.4 | 4.8 | 1.3 | 9.8 | 20.6 | 23.6 | 30.1 |
| Xylene Isomers | | | | | | | |
| Para | 30.3 | 30.8 | 33.4 | 31.4 | 32.3 | 32.5 | 31.9 |
| Meta | 20.3 | 21.4 | 21.3 | 23.3 | 24.3 | 27.9 | 35.1 |
| Ortho | 49.4 | 47.8 | 45.3 | 45.3 | 43.3 | 39.6 | 33.0 |

It will be noted from the above data that the catalyst underwent activation with time on-stream. Thus, at 300°C., conversion increased from 2.2 to 14.2% and at 400°C. from 40.5 to 54.1%.

EXAMPLES 16–44

Using a catalyst similar to those of Example 1 and containing 3.5 weight percent phosphorus, toluene and methanol were reacted under differing conditions as shown in the following Table IV:

TABLE IV

| Ex. | Temp °C | Toluene/ Methanol | Feed ml./ Hr. | WHSV | Toluene Conv. | Xylenes | | |
|---|---|---|---|---|---|---|---|---|
| | | | | | | p | m | o |
| 16 | 300 | 2:1 | 8.0 | 1.6 | 32.0 | 30 | 22 | 48 |
| 17 | 300 | 2:1 | 15.2 | 3.0 | 20.6 | 35 | 21 | 44 |
| 18 | 300 | 2:1 | 30.4 | 6.0 | 8.2 | 31.8 | 19.0 | 49.2 |
| 19 | 350 | 2:1 | 8.0 | 1.6 | 47.7 | 28 | 29 | 43 |
| 20 | 350 | 2:1 | 14.8 | 2.9 | 42.9 | 33 | 25 | 42 |
| 21 | 350 | 2:1 | 30.4 | 5.9 | 25.4 | 31 | 25 | 44 |
| 22 | 400 | 2:1 | 8.0 | 1.6 | 50.0 | 29 | 40 | 31 |
| 23 | 400 | 2:1 | 15.4 | 3.0 | 48.2 | 31 | 31 | 38 |
| 24 | 400 | 2:1 | 30.0 | 5.8 | 46.1 | 32 | 27 | 41 |
| 25 | 300 | 1:1 | 8.0 | 1.6 | 14.4 | 31 | 21 | 48 |
| 26 | 300 | 1:1 | 15.6 | 3.0 | 6.2 | 32 | 18 | 50 |
| 27 | 300 | 1:1 | 22.0 | 4.4 | 4.5 | 32 | 18.5 | 99.5 |
| 28 | 300 | 1:1 | 28.4 | 5.6 | 3.8 | 31 | 23 | 46 |
| 29 | 350 | 1:1 | 8.0 | 1.6 | 29.4 | 30 | 25 | 45 |
| 30 | 350 | 1:1 | 16.0 | 3.0 | 19.4 | 31.5 | 24 | 44.5 |
| 31 | 350 | 1:1 | 29.7 | 6.2 | 10.6 | 32 | 25 | 43 |
| 32 | 400 | 1:1 | 8.0 | 1.6 | 31.8 | 34 | 32 | 34 |
| 33 | 400 | 1:1 | 15.6 | 3.0 | 31.5 | 33 | 27 | 40 |
| 34 | 400 | 1:1 | 30.4 | 5.8 | 23.4 | 35 | 26 | 39 |
| 35 | 300 | 1:2 | 8.0 | 1.6 | 12.8 | 32 | 20 | 48 |
| 36 | 300 | 1:2 | 17.2 | 3.0 | 6.5 | 27 | 14 | 59 |
| 37 | 300 | 1:2 | 30.0 | 5.8 | 1.8 | 33 | 17 | 50 |
| 38 | 350 | 1:2 | 8.0 | 1.6 | 30.0 | 32 | 22 | 46 |
| 39 | 350 | 1:2 | 15.6 | 3.0 | 18.5 | 33 | 23 | 44 |
| 40 | 350 | 1:2 | 30.4 | 5.8 | 9.5 | 31 | 18 | 50 |
| 41 | 400 | 1:2 | 8.0 | 1.6 | 42.5 | 36 | 30 | 34 |
| 42 | 400 | 1:2 | 15.2 | 3.0 | 36.8 | 37 | 26 | 37 |
| 43 | 400 | 1:2 | 30.0 | 5.8 | 24.1 | 38 | 25 | 37 |
| 44 | 350 | 2:1 | 8.0 | 1.6 | 40 | 31 | 27 | 42 |

From the above results, it will be seen that the amounts of both para- and ortho-xylenes were enhanced and the amount of meta-xylene was diminished compared to the normal equilibrium mixture of 22 percent ortho-xylene, 24 percent para-xylene and 54 percent meta-xylene.

EXAMPLE 45

Ten grams of activated acid form of ZSM-5 (HZSM-5), prepared as in Example 1, were contacted with 75 cc of p-xylene containing 6.5 grams of $Sb(OCH_3)_3$. The resulting mixture was refluxed for 16 hours and then filtered. The separated solid was washed in turn with 100 cc of toluene, 100 cc of methanol and 100 cc of pentane. The washed product was then air-dried, placed in a vacuum oven at 115°C. for 3 hours and thereafter calcined in air at 300°C. for 1 hour. Analysis showed the resulting product contained 24 percent $Sb_2O_3$.

EXAMPLE 46

Twenty grams of activated acid form of ZSM-5 (HZSM-5), prepared as in Example 1, were contacted with 120 cc of n-octane containing 10 grams of $As(OC_2H_5)_3$. The resulting mixture was refluxed under an atmosphere of nitrogen for 16 hours and then filtered. The separated solid was air-dried for 1 hour, then dried in flowing nitrogen for 1 hour at 115°C. and finally calcined in air at 300°C. for 1 hour.

EXAMPLES 47–50

Employing the catalyst of Example 45, toluene and dimethylether were reacted utilizing a feed wherein the molar ratio of toluene to dimethyl ether was 1.4. This feed was passed over 4.0 grams of the catalyst, which had been conditioned in air at 350°C. for 1 hour, at a weight hourly space velocity of 5 at a temperature between 250° and 400°C. Results are shown in Table V below.

TABLE V

| Ex. | Temp °C | Percent Conversion of Toluene | Wt. % Selectivity | | | Xylene Isomers | | |
|-----|---------|-------------------------------|-------|------|----------|------|------|-------|
|     |         |                               | $C_8$ | $C_9$ | $C_{10}$ | Para | Meta | Ortho |
| 47  | 250     | 1.0                           | 93.8  | 6.2  | 0        | 30.5 | 18.1 | 51.4  |
| 48  | 300     | 6.4                           | 91.1  | 8.9  | 0        | 31.8 | 23.2 | 45.0  |
| 49  | 350     | 19.1                          | 82.8  | 13.9 | 3.3      | 31.3 | 24.3 | 44.4  |
| 50  | 400     | 7.8                           | 88.1  | 11.9 | 0        | 35.7 | 25.3 | 39.0  |

It will be seen from the above results that there was a selective production of ortho- and para-xylene in preference to meta-xylene utilizing the antimony modified zeolite catalyst.

EXAMPLES 51–53

Employing the catalyst of Example 46, toluene and dimethylether were reacted utilizing a feed wherein the molar ratio of toluene to dimethylether was 1.4. This feed was passed over 4.0 grams of the catalyst, which had been conditioned in air at 350°C. for 1 hour, at a weight hourly space velocity of 5 at a temperature between 250° and 350°C. Results are shown in Table VI below.

TABLE VI

| Ex. | Temp °C | Percent Conversion of Toluene | Wt % Selectivity | | | Xylene Isomers | | |
|-----|---------|-------------------------------|-------|------|----------|------|------|-------|
|     |         |                               | $C_8$ | $C_9$ | $C_{10}$ | Para | Meta | Ortho |
| 51  | 250     | 2.3                           | 93.5  | 6.5  | 0        | 30.6 | 23.0 | 46.4  |
| 52  | 300     | 3.9                           | 91.1  | 8.9  | 0        | 33.3 | 23.6 | 43.4  |
| 53  | 350     | 1.5                           | 90.5  | 9.5  | 0        | 36.4 | 25.2 | 38.3  |

The above results show that there was a selective production of ortho- and para-xylene in preference to meta-xylene utilizing the arsenic modified zeolite catalyst.

EXAMPLE 54

A 3 gram sample of HZSM-5, 1.5 grams of phenyl phosphine oxychloride and 30 milliliters of toluene were refluxed overnight. Toluene was removed by distillation under vacuum to dryness and the residue was heated in a vacuum oven overnight at a pressure of 21 millimeters of mercury at 140°C. The weight of catalyst was 4.1 grams.

A 2 gram sample of the resulting phosphorus-modified ZSM-5 catalyst was loaded in a reactor and a mixture of toluene and methanol (1 to 1 molar ratio) was contacted with the catalyst at 600°C. at a weight hourly space velocity of 11.8. The conversion of toluene was 27 percent and the ratio of para/meta/ortho xylenes was 84/11/5.

EXAMPLE 55

A mixture of three grams of large crystal HZSM-5 in 45 milliliters of toluene was refluxed for 1 hour. After cooling, 1.52 grams of trimethylphosphate were added and the mixture refluxed overnight. Toluene was distilled off and the catalyst was calcined 1 hour at 550°C.

A 1/1 molar mixture of toluene and methanol was passed over the catalyst at 550°C. at a weight hourly space velocity of 9.9. The product contained 92 weight percent para-xylene in the xylene fraction and 89 weight percent xylenes in the aromatic fraction (excluding toluene). The toluene was 17 percent converted.

EXAMPLES 56–57

Three grams of HZSM-5 and 45 ml. of toluene were refluxed for 1 hour, cooled and then 1.14 grams of trimethylphosphate were added. The resulting mixture was refluxed overnight, evaporated to dryness and thereafter calcined for 1 hour at 500°C. The catalyst so prepared contained 4.06 weight percent phosphorus.

Toluene and methanol in a molar ratio of 1 were contacted with 2 grams of the above catalyst. The reaction conditions and results are shown below in Table VII.

TABLE VII

| Ex. | Temp °C | WHSV | Conversion, % | | Wt. % Xylenes in Aromatic Products | Xylenes | | |
|-----|---------|------|---------|----------|------|------|------|-------|
|     |         |      | Toluene | Methanol |      | Para | Meta | Ortho |
| 56  | 550     | 12.1 | 17      | 87       | 82   | 86   | 8    | 7     |
| 57  | 600     | 24.1 | 16      | 80       | 92   | 98   | 2    | 0     |

EXAMPLES 58–60

Three grams of HZSM-5 and 45 ml. of toluene were refluxed for 1 hour, cooled and then 1.14 grams of trimethylphosphate were added. The resulting composite was evaporated to dryness and thereafter calcined for 1 hour at 500°C. The catalyst so prepared contained 2.39 weight percent phosphorus.

Toluene and methanol in a molar ratio of 1 were contacted with 2 grams of the above catalyst. The reaction conditions and results are shown below in Table VIII.

TABLE VIII

| Ex. | Temp °C | WHSV | Conversion, % | | Wt. % Xylenes in Aromatic Products | Xylenes | | |
|-----|---------|------|---------|----------|------|------|------|-------|
|     |         |      | Toluene | Methanol |      | Para | Meta | Ortho |
| 58  | 550     | 19.5 | 42      | 95       | 84   | 73   | 19   | 9     |
| 59  | 600     | 20.8 | 44      | 96       | 84   | 74   | 18   | 8     |
| 60  | 600     | 44.0 | 39      | 89       | 85   | 80   | 14   | 7     |

EXAMPLE 61

A mixture of 3 grams of HZSM-5 extrudate (containing 65 weight percent HZSM-5 and 35 weight percent $Al_2O_3$ binder) and 45 ml. of toluene was refluxed for 1 hour. After cooling, 2.7 grams of trimethylphosphate were added and the resulting mixture refluxed overnight. The composite obtained was evaporated to dryness and thereafter calcined for 1 hour at 500°C.

Toluene and methanol in a 1:1 molar ratio were passed over the catalyst above prepared at a temperature of 500°C. at a weight hourly space velocity of 9.3.

The weight percent xylenes in the aromatic product was 91. The para/meta/ortho xylene weight ratio was 95/1/4 at 21 percent toluene conversion. The used catalyst was found to contain 12 weight percent phosphorus. The higher phosphorus content in this catalyst in comparison to the catalyst of Example 56–60 is attributable to the presence of the alumina binder.

From the above results shown in Tables VII and VIII, and in Example 61, it will be evident that the ZSM-5 catalyst modified by the addition thereto of trimethylphosphate was highly effective in the selective production of para-xylene. Higher para-xylene selectivities were observed at 600°C. than at 550°C. Catalyst activity was inversely related and para-xylene selectivity directly related to the phosphorus content of the catalyst.

EXAMPLES 62–69

Sixty seven grams of dried HZSM-5 were combined with 26.5 grams of trimethylphosphite, $(CH_3O)_3P$ and 235 ml. of octane in a flask. The mixture was gently refluxed for 18 hours. A dry nitrogen purge was used. After cooling, the catalyst was filtered and washed with 500 ml. of methylene chloride followed by 500 ml. of pentane. The catalyst was then calcined in air at 150 ml./min. for 16 hours at a temperature of 500°C. Analysis indicated a phosphorus content of 3.45 percent by weight.

Toluene was alkylated with methanol under various conditions of reaction with this catalyst. The conditions employed and resulting conversions are shown in Table IX below.

EXAMPLES 70–78

Four grams of HZSM-5, 0.75 gram of 85% phosphoric acid ($H_3PO_4$) and 150 ml. of methanol were combined and refluxed gently for 16 hours with a nitrogen purge. The solvent was removed by distillation and the remaining catalyst heated to 250°C. in air. The catalyst was then placed in a furnace at 500°C. in air for 1 hour. Elemental analysis showed a phosphorus content of 4.45 weight percent.

Toluene was alkylated with methanol under various conditions of reaction with this catalyst. The conditions used and the resulting conversions are shown in Table X below.

TABLE X

| Example | 70 | 71 | 72 | 73 | 74 | 75 | 76 | 77 | 78 |
|---|---|---|---|---|---|---|---|---|---|
| Temp °C | 550 | 550 | 550 | 550 | 400 | 600 | 600 | 600 | 600 |
| WHSV | 10.4 | 10.4 | 10.4 | 10.4 | 10.4 | 10.5 | 16.8 | 21.9 | 42.2 |
| Toluene/Methanol (Molar Feed Ratio) | 1 | 1 | 1 | 1 | 1 | 1 | 1 | 1 | 1 |
| Stream Time (Hrs.) | 1 | 2 | 3 | 9 | 4 | 5 | 6 | 7 | 8 |
| Conv. Wt. % Toluene | 37.7 | 3.56 | 34.9 | 31.0 | 11.2 | 39.3 | 36.6 | 35.7 | 24.2 |
| Conv. Wt. % Methanol | 95.8 | 93.9 | 92.5 | 95.0 | 77.0 | 92.4 | 91.0 | 88.7 | 71.9 |
| Xylenes in Aromatic Prod. Wt. % | 73.6 | 77.2 | 80.4 | 87.6 | 80.9 | 82.8 | 87.0 | 88.4 | 90.7 |
| % Para-Xylene In Xylenes | 57.8 | 64.4 | 69.2 | 84.6 | 50.7 | 73.2 | 84.0 | 87.3 | 90.7 |

From the above results, it will be seen that the phosphoric acid-modified catalyst was effective for the production of para-xylene and that selectivity for this isomer increased significantly at higher temperature and space velocity. In addition, from a comparison of the results of Examples 70 and 73, there would appear to be a conditioning effect with time on stream which resulted in an increase in yield of para-xylene.

EXAMPLES 79–81

Four grams of HZSM-5, 2.50 gram of 85% phosphoric acid ($H_3PO_4$) and 150 ml. of methanol were combined and refluxed gently for 17 hours with a nitrogen purge. The solvent was removed by distillation and the remaining catalyst heated to 150°C. in air. The catalyst was then placed in a furnace at 500°C. in air for 1 hour. Elemental analysis showed a phosphorus content of 13.4 weight percent.

TABLE IX

| Example | 62 | 63 | 64 | 65 | 66 | 67 | 68 | 69 |
|---|---|---|---|---|---|---|---|---|
| Temp °C | 550 | 550 | 550 | 400 | 600 | 600 | 600 | 600 |
| WHSV | 10.4 | 10.4 | 10.4 | 10.4 | 10.4 | 21.9 | 44.6 | 74.0 |
| Toluene/Methanol (Molar Feed Ratio) | 1 | 1 | 1 | 1 | 1 | 1 | 1 | 1 |
| Stream Time (Hrs.) | 1 | 2 | 3 | 4 | 5 | 6 | 7 | 8 |
| Conv. Wt. % Toluene | 42.5 | 42.3 | 43.7 | 15.6 | 47.9 | 46.5 | 34.2 | 25.8 |
| Conv. Wt. % Methanol | 96.5 | 95.4 | 94.4 | 83.0 | 96.8 | 93.6 | 82.8 | 72.8 |
| Xylenes in Aromatic Prod. Wt. % | 75.2 | 76.9 | 78.4 | 81.2 | 81.9 | 84.0 | 86.8 | 89.4 |
| % Para-Xylene in Xylenes | 54.8 | 56.2 | 57.7 | 42.5 | 59.9 | 74.2 | 80.7 | 83.2 |

It will be evident from the above results that the trimethylphosphite-modified catalyst was effective for the production of para-xylene and that selectivity for this isomer increased significantly at higher temperature and space velocity.

Toluene was alkylated with methanol under various conditions of reaction with this catalyst. The conditions used and the resulting conversions are shown in Table XI below.

TABLE XI

| Example | 79 | 80 | 81 |
|---|---|---|---|
| Temp °C | 550 | 550 | 550 |

The conditions of reaction and the results obtained are shown below in Table XII.

TABLE XII

| Ex. | Temp °C | WHSV | Toluene/Methanol Molar Ratio | Total Selectivity to Xylenes | Wt % Xylene in Aromatics | Xylene Isomer Para | Xylene Isomer Meta | Xylene Isomer Ortho |
|---|---|---|---|---|---|---|---|---|
| 82 | 500 | 16.31 | 1 | 70.4 | 76.7 | 66.3 | 15.7 | 18.0 |
| 83 | 550 | 22.23 | 1 | 73.3 | 85.6 | 83.0 | 9.4 | 7.6 |
| 84 | 550 | 9.79 | 1 | 79.0 | 85.7 | 81.1 | 11.4 | 7.6 |
| 85 | 550 | 4.39 | 1 | 83.1 | 85.8 | 71.2 | 19.2 | 9.6 |
| 86* | 550 | 33.87 | .66 | 94.2 | 54.0 | 80.6 | 11.4 | 8.0 |
| 87 | 550 | 8.31 | 2 | 85.0 | 90.6 | 82.9 | 10.8 | 6.3 |
| 88 | 550 | 5.76 | 2 | 82.8 | 91.2 | 76.5 | 15.7 | 7.8 |
| 89 | 575 | 17.67 | 2 | 90.7 | 92.4 | 85.5 | 9.0 | 5.5 |
| 90 | 600 | 16.99 | 2 | 87.6 | 92.9 | 87.0 | 8.4 | 4.6 |
| 91 | 600 | 16.99 | 2 | 90.4 | 92.4 | 85.7 | 9.2 | 5.2 |
| 92 | 600 | 35.91 | 2 | 84.5 | 93.2 | 87.5 | 7.6 | 4.9 |
| 93 | 600 | 8.35 | 2 | 83.6 | 92.7 | 81.0 | 12.9 | 6.0 |
| 94 | 600 | 9.86 | 4 | 93.0 | 95.3 | 83.0 | 11.7 | 5.3 |
| 95 | 600 | 5.09 | 4 | 93.5 | 94.8 | 74.0 | 18.4 | 7.6 |
| 96 | 600 | 21.30 | 4 | 87.1 | 95.1 | 87.5 | 8.0 | 4.5 |
| 97 | 550 | 27.21 | 4 | 79.6 | 94.6 | 85.4 | 8.8 | 5.8 |
| 98 | 550 | 11.56 | 4 | 97.1 | 94.2 | 83.6 | 10.5 | 5.9 |
| 99 | 550 | 4.14 | 4 | 81.1 | 94.6 | 70.4 | 20.6 | 8.9 |
| 100 | 550 | 8.30 | 4 | 98.5 | 95.4 | 81.9 | 12.2 | 5.8 |
| 101 | 550 | 8.40 | 10 | 71.7 | 95.8 | 84.8 | 10.2 | 5.0 |
| 102 | 550 | 8.27 | 2 | 83.5 | 92.4 | 81.7 | 12.2 | 6.2 |
| 103 | 500 | 9.25 | 2 | 80.2 | 90.7 | 79.1 | 12.4 | 8.5 |
| 104 | 450 | 8.90 | 2 | 81.8 | 89.2 | 73.5 | 14.4 | 12.1 |
| 105 | 400 | 9.13 | 2 | 66.3 | 86.3 | 63.6 | 17.3 | 19.1 |
| 106 | 550 | 2.00 | 2 | 73.1 | 90.4 | 59.2 | 28.5 | 12.3 |
| 107** | 550 | 9.80 | 1.01 | 83.2 | 88.4 | 80.1 | 12.4 | 7.5 |

*Dimethyl ether used instead of methanol
**Both methanol and dimethyl ether were co-fed as the source of methyl groups [½ "CH₃O" groups as (CH₃)₂O]

TABLE XI-continued

| Example | 79 | 80 | 81 |
|---|---|---|---|
| WHSV | 10.5 | 10.7 | 10.5 |
| Toluene/Methanol (Molar Feed Ratio) | 1 | 1 | 1 |
| Stream Time (Hrs.) | 1 | 2 | 4 |
| Conv. Toluene, Wt. % | 7.2 | 9.7 | 11.4 |
| Conv. Methanol, Wt. % | 71.5 | 66.3 | 58.7 |
| Xylenes in Aromatic Prod. Wt. % | 87.2 | 89.5 | 90.5 |
| % Para-Xylene in Xylenes | 87.5 | 90.3 | 91.0 |
| Selectivity to Aromatic Products, % | | | |
| p-xylene | 76.3 | 80.8 | 82.3 |
| m-xylene | 5.5 | 4.6 | 4.4 |
| o-xylene | 5.4 | 4.1 | 3.8 |
| p-ethyltoluene | 4.1 | 3.9 | 3.6 |
| Pseudocumene | 8.7 | 6.6 | 5.9 |
| | 100.0 | 100.0 | 100.0 |

From the above results, it will be evident that the phosphoric acid-modified catalyst containing 13.4 wt. percent phosphorus was effective for para-xylene production. It will also be apparent that high selectivity to para-xylene, e.g. 90 percent at low toluene conversion, e.g. 12 percent was realized.

EXAMPLES 82-107

Five grams of HZSM-5 pellets and 75 ml. of toluene were placed in a flask and heated to reflux. There was no stirring, so as to avoid shattering the pellets and a slow stream of nitrogen was bubbled through the solution to minimize bumping. After 45 minutes, the mixture was cooled to room temperature and 4 grams of diphenyl phosphine chloride were added. Reflux was then re-established and allowed to continue for about 16 hours. The solvent was then removed by distilling to dryness. The residual solid was thereafter calcined in air at 500°C. for 1 hour.

Alkylation of toluene using the above modified HZSM-5 as catalyst was carried out by contact of toluene and methanol in a reactor zone fitted with a thermocouple and containing 0.5-3 grams of the catalyst.

From the above results, it will be evident that higher reaction temperature within the range of 400° to 600°C. afforded higher selectivity to para-xylene. Likewise, higher space velocity lead to increased selectivity to paraxylene. Increasing the toluene to methanol feed ratio at a given temperature and space velocity also served to increase the selectivity to para-xylene.

Increasing the phosphorus level in the catalyst leads to increased selectivity to para-xylene with however decreased conversion of both toluene and methanol and reduced efficiency of methanol utilization.

EXAMPLES 108-111

Catalysts of varying phosphorus content prepared in a manner similar to that utilized in Examples 82-107 were synthesized. These catalysts were used in promoting the reaction of toluene and methanol, present in a molar ratio of 1.4 (toluene/methanol) at a temperature of 550°C. The conditions and results of such reaction are shown in Table XIII below.

TABLE XIII

| Ex. | Percent Phosphorus | WHSV | Conversion Toluene, Wt. % | Percent Para-Xylene |
|---|---|---|---|---|
| 108 | 2.01 | 21.9 | 37.6 | 69 |
| 109 | 2.52 | 16.1 | 37.0 | 79 |
| 110 | 2.92 | 13.7 | 33.7 | 74 |
| 111 | 6.81 | 18.4 | 2 | 92 |

It will be seen from the above data that the selectivity with respect to para-xylene increased as the phosphorus content of the zeolite catalyst increased.

EXAMPLES 112-113

Ten grams of pelletized HZSM-5 were combined with a solution of 10 grams of diethylchloro thiophosphate, (EtO)₂P(S)Cl, and 150 ml of toluene. The suspension was gently refluxed for 18 hours over nitrogen. The solvent was distilled off and the temperature allowed to rise to 130°–140°C. The resulting catalyst was heated in an oven, in air, at 140°C. for 2 hours. Weight after this treatment was 15.0 grams. The catalyst was thenn calcined in a furnace at 500°C., in air, for a period of 4 hours. Elemental analysis revealed a phosphorus content of 5.98 percent by weight.

Two grams of this catalyst was loaded in a reactor and was contacted with a mixture of toluene and methanol (1 to 1 molar ratio) under various conditions. The results are summarized in Table XIV below.

TABLE XIV

| Example | 112 | 113 |
|---|---|---|
| Temp. °C | 550 | 600 |
| WHSV | 10.0 | 10.0 |
| Molar Feed Ratio (Toluene/Methanol) | 1 | 1 |
| Conversion, % | | |
| Toluene | 29.3 | 34.9 |
| Methanol | 94.4 | 93.2 |
| Xylenes in Aromatic Product Wt. % | 79.1 | 85.0 |
| Xylene Isomers, % | | |
| Para | 73.9 | 81.9 |
| Meta | 15.6 | 11.9 |
| Ortho | 10.5 | 6.2 |

EXAMPLES 114–115

7.91 grams of diphenylphosphinic acid, $\phi_2P(O)OH$ were dissolved in 175 ml of toluene by heating. To this solution was cautiously added 10.0 grams of pelletized HZSM-5. The white solid developed a light lemon yellow color. It was gently refluxed for 16 hours with a nitrogen sweep. The resulting solid had developed a dark brown-yellow color.

The solvent was distilled off and the temperature allowed to rise to 130°C. in nitrogen. The solid was placed in an oven at 150°C. for 1 hour. The weight was 18.00 grams at this point. The solid was then placed in a furnace at 500°C. in air for a period of 6.5 hours to give 11.2 grams of a grey white solid. Analysis revealed a phosphorus content of 4.99 percent by weight.

Two grams of this catalyst was placed in a reactor and contacted with a 1 to 1 molar mixture of toluene and methanol. The results are summarized in Table XV below.

TABLE XV

| Example | 114 | 115 |
|---|---|---|
| Temp. °C | 550 | 600 |
| WHSV | 10.0 | 10.0 |
| Feed Ratio, Molar (Toluene/Methanol) | 1 | 1 |
| Conversion, % | | |
| Toluene | 20.1 | 21.7 |

TABLE XV-continued

| Example | 114 | 115 |
|---|---|---|
| Methanol | 93.8 | 87.0 |
| Xylenes in Aromatic Product Wt. % | 78.6 | 88.1 |
| Xylene Isomers | | |
| Para | 81.2 | 91.8 |
| Meta | 10.1 | 5.0 |
| Ortho | 8.6 | 3.2 |
| Selectivity to Aromatic Products | | |
| Benzene | .2 | .2 |
| Ethyl Benzene | .4 | .4 |
| Para-Xylene | 63.8 | 81.0 |
| Meta-Xylene | 8.0 | 4.4 |
| Ortho-Xylene | 6.8 | 2.8 |
| p-Ethyl Toluene | 3.2 | 2.3 |
| Pseudocumene | 12.3 | 6.6 |
| $C_9$–$C_{10}$ Aromatics | 5.4 | 2.4 |

EXAMPLES 116–123

Ten grams of HZSM-5 were placed in a vacuum dessicator, over water, evacuated with an aspirator and allowed to stand for 16 hours. The increase in weight due to adsorption of water was 1.75 grams. The resulting catalyst pellets were then added to a solution of 8.0 grams of diphenylphosphine chloride, $\phi_2PCl$, in 150 ml of toluene and gently heated. At about 75°C., quantities of HCl were evolved as the $\phi_2PCl$ was hydrolyzed to diphenylphosphinous acid $\phi_2P(O)H$. All of the HCl was evolved when the boiling point of toluene was reached and the suspension was gently refluxed for 17 hours. The net effect of this treatment was to combine HZSM-5 with $\phi_2P(O)H$, prepared in situ. The solvent was then boiled off and the catalyst heated in an oven for 2½ hours, at 150 C., in air. It was then placed in a furnace at 500°C., in air, for 5 hours. Analysis revealed a phosphorus content of 5.08 percent by weight.

Two grams of this catalyst were placed in a reactor and contacted with various mixtures of toluene and methanol. The results are summarized in Table XVI below.

TABLE XVI

| Example | 116 | 117 | 118 | 119 | 120 | 121 | 122 | 123 |
|---|---|---|---|---|---|---|---|---|
| Temp. °C | 550 | 600 | 550 | 600 | 550 | 600 | 550 | 600 |
| WHSV | 10.3 | 10.3 | 10.5 | 10.4 | 10.5 | 10.4 | 10.4 | 10.4 |
| Time on Stream (Hrs.) | 5 | 10 | 11 | 16 | 17 | 20 | 21 | 24 |
| Feed Ratio, Molar Toluene/Methanol | 1 | 1 | 2 | 2 | 4 | 4 | 8 | 8 |
| Conversion, % | | | | | | | | |
| Toluene | 37.5 | 28.2 | 27.4 | 25.8 | 16.1 | 18.3 | 8.8 | 9.2 |
| Methanol | 98.7 | 86.8 | 99.3 | 99.4 | 99.9 | 99.9 | 99.9 | 100.0 |
| Xylenes in Aromatic Prod., % | 89.4 | 90.0 | 93.3 | 93.0 | 95.4 | 95.3 | 95.3 | 95.6 |
| Xylene Isomers, % | | | | | | | | |
| Para | 85.8 | 91.8 | 83.9 | 91.0 | 84.1 | 85.3 | 84.2 | 83.7 |
| Meta | 9.7 | 5.2 | 11.1 | 6.1 | 11.2 | 10.3 | 11.2 | 11.6 |
| Ortho | 4.6 | 3.0 | 5.0 | 3.0 | 4.7 | 4.3 | 4.6 | 4.7 |

EXAMPLES 124–127

4.00 grams of ZSM-35, uncalcined, were added to a solution of 1.50 grams of diphenyl phosphine chloride dissolved in 150 ml of toluene. The suspension, blanketed with a stream of nitrogen, was refluxed for 20 hours. The solvent was boiled down and the remaining concentrated slurry was placed in a dish and heated in an oven at 110°C. for 2 hours. A uniform powder remained which was calcined in air, in a furnace at 500°C. for 2.25 hours. The black solid weighed 3.96 grams. Analysis revealed a phosphorus content of 3.67 percent.

Two grams of this catalyst were placed in a reactor and contacted with various mixtures of toluene and methanol. The results are summarized in Table XVII. It can be seen that very high selectivities were obtained to xylenes, with unusually small amounts of higher alkylated products. The selectivity to para-xylene, especially at 600°C., was excellent.

TABLE XVII

| Example | 124 | 125 | 126 | 127 |
|---|---|---|---|---|
| Temp. °C. | 550 | 550 | 600 | 600 |
| WHSV | 9.9 | 10.3 | 10.3 | 10.4 |
| Feed Ratio, Molar (Toluene/Methanol) | 1 | 1 | 1 | 1 |
| Conversion, % | | | | |
| Toluene | 1.9 | 4.1 | 5.1 | 2.6 |
| Methanol | 13.0 | 56.4 | 46.6 | 44.9 |
| Xylenes in Aromatic Prod., % | 87.2 | 94.0 | 95.5 | 96.3 |
| Xylene Isomers, % | | | | |
| Para | 77.4 | 79.0 | 85.6 | 90.5 |
| Meta | 0 | 7.7 | 5.9 | 4.1 |
| Ortho | 22.6 | 13.3 | 8.5 | 5.4 |
| Selectivity to Aromatic Products, % | | | | |
| Benzene | 12.8 | 2.2 | 2.7 | 3.8 |
| p-Xylene | 67.5 | 74.2 | 81.7 | 87.1 |
| m-Xylene | 0 | 7.2 | 5.6 | 3.4 |
| o-Xylene | 19.7 | 12.5 | 8.2 | 5.2 |
| p-Ethyl Toluene | 0 | 3.9 | 1.8 | 0 |

It is to be understood that the foregoing description is merely illustrative of preferred embodiments of the invention of which many variations may be made by those skilled in the art within the scope of the following claims without departing from the spirit thereof.

We claim:

1. A process for the methylation of toluene such that the formation of meta-xylene is suppressed and the formation of at least one isomer selected from the group consisting of ortho- and para-xylene is enhanced which comprises contacting toluene with a methylating agent under methylation conditions in the presence of a catalyst comprising a crystalline aluminosilicate zeolite, said zeolite having a silica to alumina ratio of at least about 12, a constraint index within the approximate range of 1 to 12, said catalyst having been modified by the addition thereto of phosphorus, arsenic or antimony in an amount of at least 0.5 percent by weight.

2. The process of claim 1 wherein said addition is phosphorus.

3. The process of claim 1 wherein said addition is arsenic.

4. The process of claim 1 wherein said addition is antimony.

5. The process of claim 1 wherein said methylating agent is methanol, methyl chloride, methyl bromide, dimethylether or dimethylsulfate.

6. The process of claim 1 wherein said crystalline aluminosilicate zeolite is characterized by a silica/alumina ratio is excess of 30.

7. The process of claim 1 wherein said crystalline aluminosilicate zeolite is ZSM-5.

8. The process of claim 1 wherein said crystalline aluminosilicate zeolite is ZSM-11.

9. The process of claim 1 wherein said methylating agent is methanol.

10. The process of claim 2 wherein phosphorus addition is accomplished as a result of contact of the crystalline aluminosilicate zeolite with a phosphorus compound.

11. The process of claim 10 wherein said phosphorus compound is trimethylphosphite.

12. The process of claim 10 wherein said phosphorus compound is diphenyl phosphine chloride.

13. The process of claim 10 wherein said phosphorus compound is phosphoric acid.

14. The process of claim 10 wherein said phosphorus compound is diphenyl phosphinous acid.

15. The process of claim 10 wherein said phosphorus compound is trimethylphosphate.

16. The process of claim 1 wherein said addition is present in an amount of between about 0.5 and about 25 weight percent.

17. The process of claim 3 wherein arsenic addition is accomplished as a result of contact of the crystalline aluminosilicate zeolite with an arsenic compound.

18. The process of claim 17 wherein said arsenic compound is arsenic triethoxide.

19. The process of claim 4 wherein antimony addition is accomplished as a result of contact of the crystalline aluminosilicate zeolite with an antimony compound.

20. The process of claim 19 wherein said antimony compound is antimony trimethoxide.

21. The process of claim 1 wherein said crystalline zeolite is ZSM-21.

22. The process of claim 1 wherein said crystalline zeolite is ZSM-35.

23. The process of claim 10 wherein said phosphorus compound is diphenylphosphinic acid.

24. The process of claim 10 wherein said phosphorus compound is diethylchloro thiophosphate.

* * * * *

UNITED STATES PATENT AND TRADEMARK OFFICE
CERTIFICATE OF CORRECTION

PATENT NO. : 3,965,208
DATED : June 22, 1976
INVENTOR(S) : STEPHEN A. BUTTER and WARREN W. KAEDING It is certified that error appears in the above-identified patent and that said Letters Patent are hereby corrected as shown below:

Column 2, line 51, "conductive" should be --conducive--.

Column 6, line 11, "528,06" should be --528,061--.

Column 6, line 11, "November 12, 1974" should be --November 29, 1974--.

Signed and Sealed this

Sixteenth Day of November 1976

[SEAL]

Attest:

RUTH C. MASON
Attesting Officer

C. MARSHALL DANN
Commissioner of Patents and Trademarks